United States Patent
Fouillet et al.

(10) Patent No.: US 7,404,930 B2
(45) Date of Patent: Jul. 29, 2008

(54) METHOD AND SYSTEM FOR PERFORMING IN CONTINUOUS FLOW A BIOLOGICAL, CHEMICAL OR BIOCHEMICAL PROTOCOL

(75) Inventors: Yves Fouillet, Voreppe (FR); Raymond Charles, St Jean de Moirans (FR); Nicolas Sarrut, Seyssine Pariset (FR); Patricia Claustre, Moirans (FR)

(73) Assignee: Commissariat a l'Energie Atomique, Paris (FR)

( * ) Notice: Subject to any disclaimer, the term of this patent is extended or adjusted under 35 U.S.C. 154(b) by 493 days.

(21) Appl. No.: 10/466,106

(22) PCT Filed: Jan. 25, 2002

(86) PCT No.: PCT/FR02/00309

§ 371 (c)(1),
(2), (4) Date: Jul. 21, 2003

(87) PCT Pub. No.: WO02/061438

PCT Pub. Date: Aug. 8, 2002

(65) Prior Publication Data

US 2004/0053418 A1    Mar. 18, 2004

(30) Foreign Application Priority Data

Jan. 29, 2001   (FR) .................................. 01 01159

(51) Int. Cl.
*B01L 3/02*    (2006.01)
*G01N 1/10*    (2006.01)

(52) U.S. Cl. ............................ 422/100; 422/50; 422/63; 422/64; 422/65; 422/66; 422/67; 422/68.1; 436/180; 436/43; 436/44; 436/47

(58) Field of Classification Search ................. 422/100, 422/50, 63–67, 68.1; 436/180, 43–44, 47
See application file for complete search history.

(56) References Cited

U.S. PATENT DOCUMENTS

| | | | |
|---|---|---|---|
| 3,368,872 A | 2/1968 | Natelson | |
| 3,566,677 A | 3/1971 | Cole et al. | |
| 4,349,510 A | 9/1982 | Kolehmainen et al. | |
| 4,883,642 A | 11/1989 | Bisconte | |
| 5,446,263 A | 8/1995 | Eigen et al. | |
| 5,508,200 A | 4/1996 | Thayer et al. | |
| 5,736,106 A | 4/1998 | Ishiguro et al. | |
| 6,783,732 B2 * | 8/2004 | Madden et al. | ............... 422/63 |
| 2002/0012611 A1 * | 1/2002 | Stylli et al. | ................... 422/65 |
| 2003/0113233 A1 * | 6/2003 | Nanthakumar | ............... 422/100 |

(Continued)

FOREIGN PATENT DOCUMENTS

EP    0 723 812    7/1996

(Continued)

Primary Examiner—Brian R. Gordon
(74) Attorney, Agent, or Firm—Oblon, Spivak, McClelland, Maier & Neustadt, P.C.

(57) ABSTRACT

The invention concerns the performing, in continuous flow, of a biological, chemical or biochemical protocol on substances to be analysed, comprising several steps which consists in: in causing a mobile analysis support (11) comprising means (12) for receiving substances to be analysed and reagents to move past; implementing the steps of the protocol on the substances as the mobile analysis support (11) moves past.

27 Claims, 2 Drawing Sheets

U.S. PATENT DOCUMENTS

2003/0124735 A1 * 7/2003 Nanthakumar et al. ...... 436/180

FOREIGN PATENT DOCUMENTS

| | | |
|---|---|---|
| JP | 4-501530 | 3/1992 |
| JP | 8-196299 | 8/1996 |
| JP | 9-224644 | 9/1997 |
| WO | 95 34374 | 12/1995 |
| WO | 99 11373 | 3/1999 |
| WO | 99 34920 | 7/1999 |
| WO | 01 51207 | 7/2001 |

* cited by examiner

METHOD AND SYSTEM FOR PERFORMING IN CONTINUOUS FLOW A BIOLOGICAL, CHEMICAL OR BIOCHEMICAL PROTOCOL

TECHNICAL FIELD

This invention relates to a process and system for performing a biological, chemical or biochemical protocol in continuous flow. It is a means of performing a complete analysis protocol on a large number of samples.

STATE OF THE PRIOR ART

For biological studies, there is a need to perform chemical, biochemical or biological reactions according to a clearly defined protocol. These reactions very frequently include mixing steps, heat treatment steps, incubation steps and detection steps.

For example, the system may be used for the synthesis of fine chemicals, in other words chemicals made in small quantities, and/or with a very high quality, or series of steps involving a treatment of reagents and/or injection of reagents. The system may also be used for tracking drugs, for example when a drug is bonded to a target protein, or for biological analyses such as the detection of a protein—protein interaction or the detection of a component containing proteins in a complex biological sample.

The PCR (Polymerisation Chain Reaction) process is very widely used in genetics as an example of a chemical or biological reaction. A Polymerisation Chain Reaction (PCR) step requires mixing a DNA sample with reagents necessary for amplification. The reaction volumes then have to be passed through temperature cycles with temperatures of between 50° C. and 94° C.

Machines capable of optimising the following points have to be designed, in order to increase the cost effectiveness of laboratory installations:

minimise volumes of samples and reagents to minimise the cost of implementing reactions, bring several reactions into series in the same system, the ideal solution being to perform an entire biological protocol on the same machine, carry out a large number of analyses in parallel, which increases the capacity of laboratories (in terms of the number of analyses per day and per machine).

At the present time, there are two major families of machines for performing a complete chemical or biological analysis protocol for a large number of samples. A first family is composed of systems in which liquids are deposited in wells. A second family is composed of micro-systems in which fluids are transferred in micro-channels. The terms µTAS for "Total Analysis System" and µFIA for "Flow Injection Analysis" are also used.

For the first family of machines, the biological sample is placed in a reservoir formed in a plate and in the shape of a well that is heated in sequence to the required temperatures for the heat treatments necessary for the biological reactions. Commercial instruments like those produced by the M.J. Research company or by the Perkin Elmer company usually use a thermostat-controlled system based on the Peltier effect. This method is easy to implement and components are standardized in the case of titration plates with 384 wells distributed according to a matrix of 16 rows and 24 columns.

Each operation in the biological protocol (filling, PCR, addition of a reagent) is usually made on different machines. The samples, reagents and plates may become very complicated to manage, depending on the number of analyses to be made. It is not possible to work with a continuous reaction flow with this type of machine, since machines are usually only capable of treating a single plate at a time.

With the second family of machines, which is more recent than the first family, micro-channels are used to transport liquids necessary for the reactions. There are many advantages of this second family, for example:

miniaturisation of volumes of reagents and samples, integration of several reactions on the same component, which enables a complete biological protocol to be performed on the same biochip, which minimizes or facilitates automation of manipulation operations, performing protocols on several channels in parallel.

The channels may be obtained by etching in substrates made of silicon, glass or a polymer material. The liquids involved in the reaction circulate through controlled temperature zones. Further information about this subject can be obtained in the article "Continuous Flow PCR on a Chip" by M. U. KOPP et al., Proceedings of the µTAS'98 Workshop, Banff, Canada, Oct. 13-16, 1998, Ed. Kluwer Academic Publishers, pages 7 to 10.

There are also systems in which several samples circulate at the same time on the same channels. This is referred to as a continuous reactions flow. Further information about this subject can be obtained in the article "Synthesis and Analysis of Chemical Components in Nanoscale" by E. LITBORN et al., Proceedings of the µTAS'2000 symposium, pages 447 to 454, and in international application WO-A-00/21 666.

Unfortunately, it is difficult to perfect these components, mainly due to the problem of controlling the transport of liquids in channels. Forcing liquids to move requires integrated pumping methods such as electro-osmosis or high pressure or imposed flow distribution systems that are difficult to perfect and often have a very high manufacturing cost. The pumping function to transport liquids in the channels in which the protocol reactions are performed, is a key and inescapable aspect of all "lab on a chip" components.

American Pat. No. 5,736,106 discloses a device for performing a heat treatment protocol on a substance. The device comprises a heat conducting plate with cavities that act as reaction chambers and that contain a substance to be analysed. The reaction chambers are closed off by a transparent sheet. A conveyor belt mechanism brings the plate with cavities to successive fixed positions to increase the temperature of the contents of the cavities to determined temperatures.

PRESENTATION OF THE INVENTION

The invention combines the advantages of state of art techniques while minimizing the disadvantages. It makes it possible to work in a continuous analysis flow on the same machine in order to increase the cost effectiveness of laboratories. It is a means of carrying out all steps in a biological protocol on one machine, integrating injection of reagents or samples, mixing of reagents, detection of analytes, optical or heat treatments or the implementation of functions such as temperature cycling, reagent mixes and possibly detection. It does not necessitate the development of complex liquid pumping systems in micro-channels.

The invention uses an analysis support that moves continuously or in small steps. Unlike American Pat. No. 5,736,106 mentioned above, the steps in the protocol may be made simultaneously on a large number of samples, so that the biological protocols can be performed continuously.

A first purpose of the invention consists of a system to perform biological, chemical or biochemical protocols on substances to be analysed in continuous flow, the system comprising:
- a mobile analysis support comprising means of reception of substances to be analysed and reagents, the reception means being arranged so as to form a matrix of rows and columns,
- means of implementing the protocol, arranged so that the support reception means pass in front of them while this protocol is being implemented, characterised in that:
- the mobile analysis support is provided with means of preventing evaporation of substances to be analysed and reagents,
- the means of preventing the evaporation of substances to be analysed and reagents are chosen from among:
  - a liquid medium that is immiscible with the substances to be analysed, reagents and products created in the reaction between substances to be analysed and reagents,
  - a liquid film immiscible with the substances to be analysed and reagents, covering the reception means and through which the substances to be analysed and reagents can pass,
- the means of implementing the protocol include successive means of inputting different energies.

It may also comprise means of delivering the substances to be analysed and reagents sequentially to the mobile analysis support reception means. It may also comprise detection means applied to substances on which the protocol has been performed to provide an analysis of these substances.

The means of implementing these steps in the protocol may also comprise means of injecting a reagent or a sample, means for optical treatment (for example an ultraviolet treatment) of a reagent or a sample, means of applying a magnetic field, suction means to remove all or some of a reaction volume, detection means, for example to detect a parameter of a constituent of a sample or any other detectable marker, and chemical treatment means for a sample.

Means of inputting energy may be heating means to heat the reception means to a determined temperature. These heating means may comprise at least one thermal rod at said determined temperature. The thermal rod may heated to said determined temperature by circulation of a heat transporting fluid and/or by Joule effect and/or the Peltier effect and/or light radiation. The system may also comprise means of bringing the mobile analysis support close to the thermal rod.

According to one example embodiment, the means of conveying the substances to be analysed and the reagents, and the means of implementing the protocol are arranged so as to obtain the following, in sequence:
- bringing a first chemical compound in a reaction volume to the reception means,
- displacement of the mobile analysis support towards a first injection element,
- bringing a second chemical compound into the reaction volume through the first injection element,
- and optionally, displacement of the mobile analysis support towards a second injection element to add a third chemical compound to the reaction volume.

The detection means may be means that supply an analysis of substances directly on the mobile analysis support or means supplying an analysis of substances after they have been transferred from the mobile analysis support.

According to one variant embodiment, the mobile analysis support consists of a plate, the reception means being composed of pads arranged on a face of the plate and used to attach the substances to be analysed.

According to another variant embodiment, the mobile analysis support is a film. The reception means may depend on capillarity forces between a surface of the film and the substances to be analysed. The film may be free to move between an unwinder reel and a winder reel. If the film is a uniform film, the film surface may be a hydrophilic surface. The film may be a structured film, the structure of the film determining the location of the reception means. For example, the film surface may be hydrophobic and may support hydrophilic pads forming the said reception means. The film may have an anisotropic thermal conductivity, the thermal conductivity through the thickness of the film being greater than the thermal conductivity in the plane of the film.

A second purpose of the invention is a process for performing a biological, chemical or biochemical protocol in continuous flow, on the substances to be analysed, the process being characterised in that it comprises:
- moving a mobile analysis support comprising means of reception of substances to be analysed and reagents, the reception means being arranged so as to form a matrix of rows and columns, the mobile analysis support being provided with means of preventing evaporation of substances to be analysed and reagents chosen from among:
  - a liquid medium that is immiscible with the substances to be analysed, the reagents and reaction products between substances to be analysed and reagents,
  - a liquid film that is immiscible with the substances to be analysed and the reagents, covering the reception means and through which the substances to be analysed and reagents may pass,
- implementation of the protocol on substances to be analysed while the mobile analysis support is moving, due to the use of successive means of adding different energies.

Advantageously, the substances to be analysed and the reagents are brought successively to the different reception means of the support as it moves.

The process may also include an analysis of substances on which the protocol was performed, by detection means.

The energy input step may consist of adding thermal energy.

According to one particular embodiment, the process takes place so as to obtain the following in sequence:
- bringing a first chemical compound in a reaction volume as far as the reception means,
- displacement of the analysis support to a first injection element,
- bringing a second chemical compound in the reaction volume by the first injection element,
- and optionally, displacement of the mobile analysis support towards a second injection element to provide a third chemical compound to the reaction volume.

The substances on which the protocol was performed can be analysed directly on the mobile analysis support or after their transfer from the mobile analysis support.

BRIEF DESCRIPTION OF THE DRAWINGS

The invention will be better understood and other advantages and specific features will become clear after reading the following description, given as a non-limitative example, accompanied by the appended drawings, wherein.

DETAILED DESCRIPTION OF EMBODIMENTS OF THE INVENTION

Figure 1:
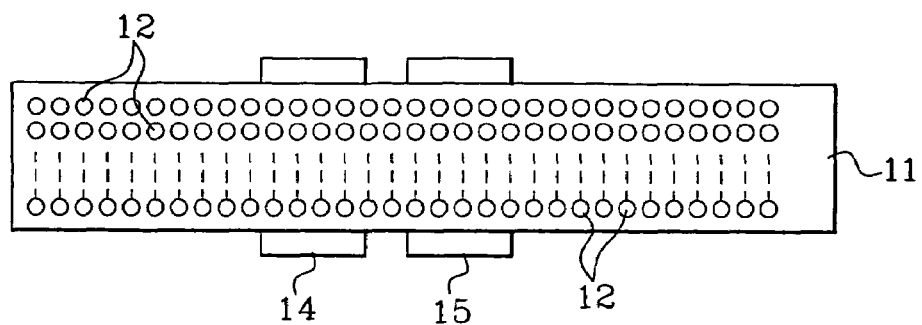
FIG. 1 is a top view of a system for performing a biological, chemical or biochemical protocol according to the invention, in continuous flow.

As described above, the system may also advantageously be used for any application involving a protocol comprising steps in series. The means of implementing a protocol may for example include means of injecting a reagent or a sample, means of optical treatment (for example ultraviolet treatment) to a reagent or a sample, detection means for example to detect a parameter of a constituent of a sample or any detectable marker, and means of applying a heat treatment to a sample.

In particular, any synthesis requiring series injection of reagents may be advantageously implemented according to the process, and using the system according to the invention. For example, applications of the invention include the synthesis of chemicals, particularly fine chemicals, in other words made in small volumes and/or with a very high quality. Furthermore, a microfluidic substrate or a device according to the invention and using more than one protocol could be designed, for example for the synthesis of fine chemicals in combination with in-line tracking (for example tracking of drugs).

In one application of the invention, one or several reagents are arranged on the surface of the support as required, in the form of a liquid droplet. Other reagents may be added by injection elements placed along the device, these injection elements injecting the required quantity of reagents. The characteristics of the device, comprising the material from which the analysis support is made and other materials, are chosen to be compatible with the characteristics of the envisaged reactions, for example the temperatures of reactions and solvents (for example water, organic solvents) used in the synthesis. In another embodiment, the system according to the invention may be used for tracking drugs in which a protein or a cell composition is supplied to the support in the form of a droplet, a test compound is injected by an injection element positioned along the system, and optionally a detection or analysis step is carried out on the sample, preferably by detection means located on the system. In another embodiment, the system may be used for a detection protocol in which a sample is supplied to the analysis support in the form of droplets and an element is positioned in the system to carry out a detection step. For example, laser nephelometry may be used to detect antigen-antibody complexes for high flow tracking to determine the solubility of a drug in water. Further information about this subject can be obtained in the article by C. D. BEVAN et al., published in Anal. Chem., Apr. 15, 2000, 72(8), pages 1781 to 1787. In other applications, means of performing ultraviolet treatment are used to implement the protocol. For example, ultraviolet light is known for its property of inducing cross-linking between complementary DNA strands and between DNA and proteins. A sample is provided to the analysis support in the form of a droplet and an ultraviolet treatment element included in the system is used to treat the sample, as for a targeted gene modification on the triple spiral (see article by F. X. BARRE et al., published in Proc. Natl. Acad. Sci. USA, Mar. 28, 2000, 97(7), pages 3084 to 3088), for cross linking of proteins to DNA in human cell nuclei (see article by S. LEJNINE, published in Nucleic Acids Res., Sep. 15, 1999, 27 (18), pages 3676 to 3684), for inactivation of pathogenic elements (see article by M. GHALI et al., published in J. Neurovirol, October 1998, 4 (5), pages 521 to 530). In other applications of the invention, the means of implementing a protocol comprise an area in which a magnetic field is applied, as for the separation of constituents of a sample by association with magnetic beads (for example purification by calibration for sequencing applications using paramagnetic particles, G. FRY et al., Biotechniques, Jul. 1992, 13(1), pages 124 to 131). In other applications of the invention, the means of implementing a protocol comprise extraction means that can be used to extract a determined volume of a sample or a fraction of a sample. In other applications, the means of implementing a protocol involve thermal elements to increase the temperature of a sample to a determined value, for example to perform a PCR reaction as will be described later.

FIG. 1 shows a first mobile analysis support 11 placed in the system according to the invention. The support 11 is a film supporting a matrix of drops 12 forming the different reaction media in which chemical reactions will be carried out when the reagents are added. The analysis support is linked to a mechanism for creating a movement, along the direction of the arrow, to enable forwards movement of each column of drops with respect to the different elements necessary for performing the protocol.

Some protocols such as PCR require temperature cycling, typically about twenty cycles at 94° C. (denaturing) –55° C. (hybridising) –72° C. (elongation) with constant temperatures lasting for a few tens of seconds. These temperature variations are imposed by temperature control elements like those referenced 14 and 15 in FIG. 1, also called temperature rods and for example operating by the Peltier effect or by circulation of a heat transporting fluid.

The heat transporting fluid may circulate through a circular channel passing through the thermal rods, or through a system of ribs for optimising heat exchanges between the heat transporting fluid and the rod. Each of the thermal rods is connected to a thermostat-controlled bath with a pumping system to circulate the heat transporting fluid.

Temperature measurement elements can be integrated into rods to servocontrol the temperature of the thermostat-controlled bath. Complementary heating elements can also be integrated into the thermostat controlled rods. For example, the heating element may be an electrical resistance acting as a heat source and the heat transporting fluid as a cooling source. Heating may be applied by light radiation.

It may be useful to add a system to press the analysis support onto the heating rod, in order to increase heat exchanges. For example, this may be achieved using a suction system at the heating rod or by a flange system, the analysis support being sandwiched between the flange and the heating rod.

It may be particularly advantageous if the belt or the film is placed in a containment filled with a liquid immiscible with the products that will be added, before use, to prevent the evaporation of substances to be analysed and reagents. These different products may be conveyed through small capillaries arranged so that the products to be injected are added successively while the analysis support is moving. For example, the capillaries may be molten silica fibres frequently used in microfluidic devices. For example, the formation of a drop at the exit from the fibre may be controlled by a pressure generator or by a syringe pusher.

Figure 2:
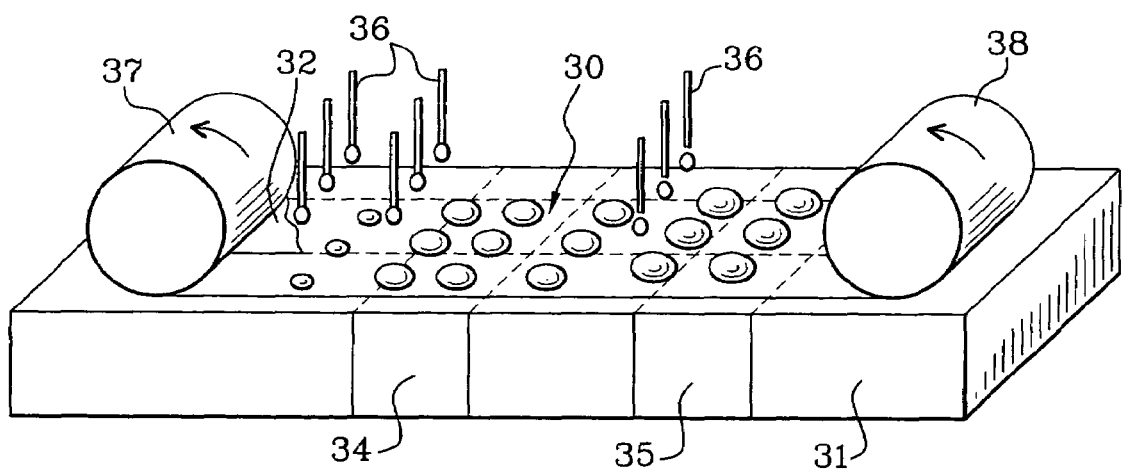
FIG. 2 is a perspective view of a mobile analysis support according to the invention while the system is in operation.

In the embodiment shown in FIG. 2, the mobile analysis support is a film 30 or a conveyor belt. The substances to be analysed and the reaction products correspond to drops deposited on the moving film 30. FIG. 2 shows injection capillaries 36 and temperature control elements 34 and 35 housed in a board 31.

The drops are attached by capillarity forces between the drops and the film 30. A film translation system transports the drops along the different elements so that the protocol can be performed (deposits, heating, detection). In the example shown in FIG. 2, the film 30 is moved by a winding system similar to a VCR cassette, the film passing from an unwinder reel 37 or to a winder reel 38.

The unwinding film 30 is covered by an oil film 32 or a liquid that is immiscible with the substances to be analysed and the reagents, so that they cannot evaporate. The liquid that is immiscible with the substances to be analysed and the reagents may be oil (mineral, silicone) or an organic solvent that is immiscible with water, such as octane.

Obviously, the example embodiment illustrated in FIG. 2 can comprise several series of heating areas to perform the required cycles, for example a PCR cycle.

The film may either be uniform or structured. In the case of a uniform film, it is advantageous if the film is slightly hydrophilic so that the deposited drop does not roll and to assure that the drop bonds to the film. It is possible to use a film made of an organic material (a plastic or a polyamide such as Kapton®) or a metallic thread (for example made of aluminium and gold).

The advantage of a structured film is that it can act on self-positioning of the drops. For example, this may be done by a hydrophobic film with hydrophilic pads. Drops are then positioned by capillarity on hydrophilic pads. It is also possible to obtain the same result by structuring the film with basins.

It is also possible to use films with an anisotropic thermal conductivity, in other words thermally insulating in the plane of the film and thermally conducting through its thickness, in order to optimise heat exchanges and to minimise heat flows between the temperature control elements.

The consumable part of the system is then reduced to a film that has the advantage of being easier and less expensive to make than well or channel structures.

Furthermore, the visibility of the drops enables a real time check and measurement of reaction volumes after each injection, which can be useful for developing real time production monitoring.

Figure 3:
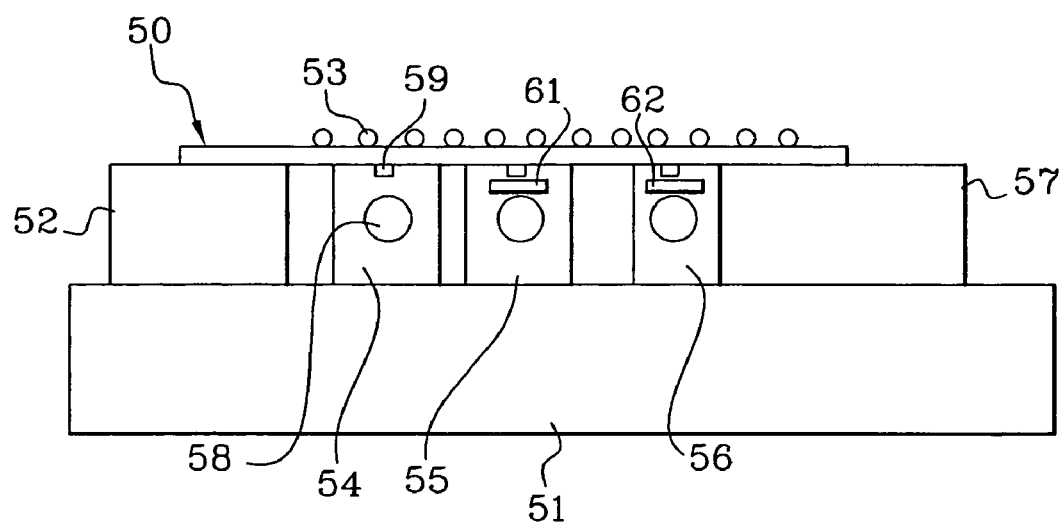
FIG. 3 shows a longitudinal sectional view showing a partial view of the system according to the invention showing three thermal rods that are used to carry out the steps of a biological, chemical or biochemical protocol.

FIG. 3 shows temperature control elements. A frame 51 supports a board 52 on which a mobile analysis support 50 moves. Reaction volumes 53, in the form of drops, are arranged uniformly on the analysis support 50. FIG. 3 shows three temperature control elements 54, 55 and 56. These elements are thermal rods housed in an insulating material 57, their upper face flush with the insulating material. Other heating means may be used, for example based on the Joule effect, the Peltier effect, or the effect of light radiation. The thermal rods 54, 55 and 56 are provided with a hole for passing a heat transporting fluid, such as hole 58. Their upper face is provided with a suction cavity, such as cavity 59 on the thermal rod 54, connected to the intake device in order to push the analysis support 50 into contact onto the thermal rods. The thermal rod 55 has an electrical resistance 61 to increase the temperature of this rod. The thermal rod 56 comprises an element 62 for measuring the temperature of the top face of this rod.

Figure 4:
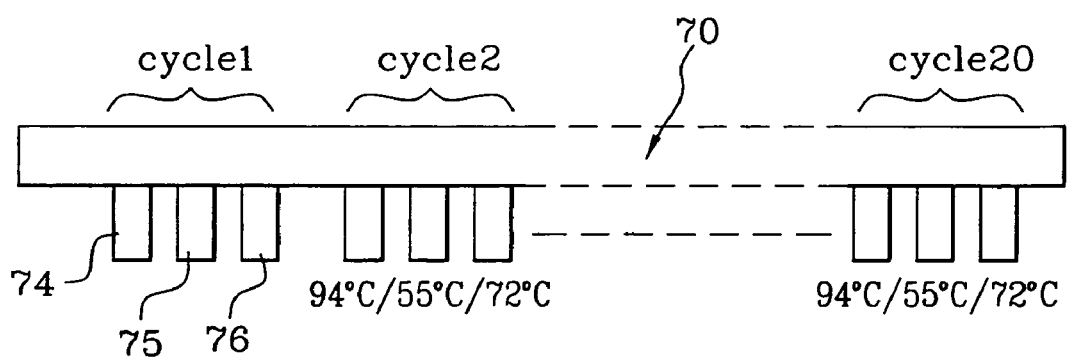
FIG. 4 illustrates a PCR cycle performed on a mobile analysis support in accordance with the invention.

FIG. 4 diagrammatically shows a mobile analysis support 70 subjected to a 20-cycle protocol PCR. Each cycle comprises submission of a substance to the three separate temperatures 94° C., 55° C. and 72° C. in sequence, supplied by twenty groups of thermal rods 74, 75 and 76.

The advantage of the invention compared with techniques according to the prior art can be demonstrated using a protocol for the analysis of a series of samples comprising the following steps:

mix a first reagent with a sample,
thermal cycling with a duration $t_1$,
addition of a second reagent,
thermal cycling for a duration $t_2$,
addition of a third reagent,
detection of a substance, with a different colour or physicochemical magnitude.

With the invention, this protocol can be carried out for a large number of samples (for example 384) combined with a large number of different reagents (for example 100). The invention can be used to obtain these 100×384 analyses in a shorter time than would be possible with machines using plates with traditional wells, while maintaining a simpler embodiment than "lab on a chip" systems. With standard machines using plates with 384 wells, the protocol implementation time is $100 \times (t_1 + t_2)$. This time is incompressible, and is usually too long. It is also necessary to design robots for manipulating 100 well plates, together with a system for management and distribution of 100×384 samples and 3×100×384 reagent distributions.

With a machine using micro-channel chips operating in a continuous reaction flow, the system can be sized to minimize the time necessary for the 100×384 reactions using the continuous flow system. For example, all that is necessary is to make a chip with 384 channels and to circulate the 100 reactions, one after the other, in each of the 384 channels on the different areas in which the steps of the protocol are carried out, each reaction being separated from the others by miscible or immiscible separator plugs (see document WO-00/21 666). The time necessary for the 100×384 reactions is given by the time for the passage between two successive reactions. Thus, a very high liquid velocity will mean that all reactions can be circulated in a minimum time.

The liquid displacement velocity V is controlled by relation V=L/t, where L is the length of the zones in which the biological protocols are carried out, and t is the time of the biological protocols. It is then possible to use long lengths to increase the reaction displacement velocity and therefore to minimize the time necessary to obtain the 100×384 reactions. However, this observation creates a problem, since the need to increase the length of the channels is contrary to miniaturization of the microfluidic chip and jeopardises the use of microtechnologies for making the component. Furthermore, control of displacements on 384 channels in parallel with the 100 different reactions creates a major design problem and in particular, the problems of fluid mechanics in small channels have to be perfectly controlled.

With the invention, the advantage of a continuous reaction flow can be maintained, in terms of the speed of execution of the 100×384 reactions, without the disadvantage of control over the displacement of liquids in the micro-channels. With the invention, biological reactions can be carried out in continuous flow, by moving the mobile support on which the reaction volumes are immobilised. Therefore, the displacement of reaction volumes is directly controlled by displacement of the mobile support, which is much easier than a pumping system in micro-channels. Note also, another advantage compared with micro-channel devices, is that the displacement velocity of the analysis support, and consequently of the analysed samples, is independent of the volumes of samples or injected volumes.

We will now give an example of the use of the principle of the invention to perform a PCR protocol.

The mobile analysis support is a 200 HN Kapton film available from Dupont, and is 50 μm thick. The immiscible liquid used is a light type of mineral oil available from Sigma.

A 100 μl PCR solution may comprise the following constituents, which provide an illustration of possible samples:

10 μl of 10× buffer (Gibco),
4 μl of magnesium Mg2+ (Gibco) 50 mM,
10 μl of dNTP (dATP, dCTP, dGTP, dTTP) 2 mM,
twice 4 μl of primers,
10 μl of BSA 20 mg/ml,
58 μl of coloured water to clearly display the drops,
1 μl of matrix (DNA),
2 μl of taq polymerase (Gibco).

Drops of this solution are deposited on the belt or film, using oil.

The drops, with a volume of 0.5 μl, 1 μl and 2 μl, are then subjected to about thirty heat cycles at successive temperatures of 94, 55 and 72° C. in accordance with the invention. After recuperation of the drops, the results are analysed by electrophoresis on an agarosis gel. The results obtained are compared with the results obtained using a control resulting from amplification by PCR of a 2 μl volume of the same preparation, but amplified on a standard well plate type apparatus.

One variant of the previous protocol consists of depositing a first 0.5 μl drop containing DNA and then a second deposit of a 0.5 μl drop containing the primers. The operations may also be done in parallel by making a column of N drops containing different types of DNA. Thus, N rows of 0.5 μl drops are formed, and the 0.5 μl drops of reagents containing the primers are then deposited in sequence. The primers are different for each column. Thus, amplifications by PCR can be made on N different types of DNA, for a large number of different primers.

The different tests carried out on the invention have reached the following conclusions.

The shape of the drops is reproducible. Each drop, once attached to the film by capillarity forces, remains fixed to the film with very good stability throughout the process for performing the biological protocol.

The mix between the two 0.5 μl volumes is very fast and there is no need to add an additional function to force the mix, unlike the disclosures in document WO-A-95/34 374. It has been observed that with small volumes (of the order of 1 μl), the mix is made in a few seconds.

The thermal cycles are applied to the drops with sufficient precision for a PCR protocol. The presence of oil and the film does not disturb heat exchanges between the reagents and the different thermal rods.

The system composed of the Kapton® film and mineral oil with the described configuration is biocompatible for a PCR.

A gas bubble may appear after a few thermal cycles. However, this does not detract from the result. Therefore, there is no need to perform degassing operations for the various liquids before performing PCR cycles.

The invention claimed is:

1. A system to perform a biological, chemical or biochemical protocol in continuous flow on substances to be analysed comprising:
   a mobile analysis support comprising means of reception of substances to be analysed and reagents, wherein the reception means are arranged so as to form a matrix of rows and columns;
   a mechanism connected to the support, where the mechanism moves with a continuous movement or in small steps thereby enabling each column in the reception means to pass in front of one or more different elements necessary to perform the protocol;
   a liquid film covering the reception means, where the liquid film is immiscible with the substances to be analysed and the reagents, thereby preventing the evaporation of the substances to be analysed and the reagents;
   means of delivering the substances to be analysed to the reception means,
   means of delivering the reagents to the reception means; and
   heating means arranged such that, while the protocol is being carried out, each column in reception means passes in front of the relevant heating means and delivery means, the arrangement of heating means and delivery means being set up in accordance with said protocol, thereby bringing the reception means to different determined temperatures successively, wherein
   the means of delivering the reagents is between the means of delivering the substances to be analysed and the heating means.

2. The system according to claim 1, further comprising detection means for the substances on which the protocol has been performed, thereby providing an analysis of these substances.

3. The system according to claim 1, wherein the heating means comprises at least one thermal rod brought to said determined temperature.

4. The system according to claim 3, wherein the thermal rod is brought to said determined temperature by circulation of a heat transporting fluid and/or by Joule effect and/or the Peltier effect and/or light radiation.

5. The system according to claim 3, further comprising means for bringing the mobile analysis support close to the thermal rod.

6. The system according to claim 1, wherein the different elements necessary to implement the protocol are arranged so as to obtain the following, in sequence:
   bringing a first chemical compound into a reaction volume to the reception means,
   displacement of the mobile analysis support towards a first injection element,
   bringing a second chemical compound into the reaction volume through the first injection element,
   and optionally, displacement of the mobile analysis support towards a second injection element to add a third chemical compound to the reaction volume.

7. The system according to claim 2, wherein the detection means are means that provide an analysis of substances directly on the mobile analysis support.

8. The system according to claim 2, wherein the detection means are means providing an analysis of substances after they have been transferred from the mobile analysis support.

9. The system according to claim 1, wherein the mobile analysis support is in the form of a plate, the reception means comprises pads arranged on a face of the plate and the reception means is used to attach the substances to be analysed.

10. The system according to claim 1, wherein the mobile analysis support is a film.

11. The system according to claim 10, wherein the reception means are provided by capillarity forces between a surface of the film and the substances to be analysed.

12. The system according to claim 10, characterised in that the film is free to move between an unwinder reel and a winder reel.

13. The system according to claim 10, wherein the film is a uniform film, and a surface of the film is hydrophilic.

14. The system according to claim 10, wherein the film is a structured film, and the structure of the film can be used to determine the location of the reception means.

15. The system according to claim 14, wherein a surface of the film is hydrophobic and supports hydrophilic pads forming said reception means.

16. The system according to claim 10, wherein the film has an anisotropic thermal conductivity, whereby the thermal conductivity through the thickness of the film is greater than the thermal conductivity in the plane of the film.

17. A process for performing a biological, chemical or biochemical protocol in continuous flow on substances to be analysed, wherein said process is carried out with a system according to claim 1, and said process comprises:
   moving the mobile analysis support,
   implementing the protocol on substances to be analysed while the mobile analysis support is moving, by the input of the thermal energy supplied by the heating means.

18. The process according to claim 17, wherein the substances to be analysed and the reagents are brought successively to different reception means of the support as it moves.

19. The process according to claim 17, further comprising analyzing substances on which the protocol was performed by a detection means.

20. The process according to claim 18, comprising the following steps in sequence:
   bringing a first chemical compound in a reaction volume as far as the reception means,
   displacement of the analysis support to a first injection element,
   bringing a second chemical compound into the reaction volume by the first injection element,
   and optionally, displacement of the mobile analysis support towards a second injection element to bring a third chemical compound into the reaction volume.

21. The process according to claim 19, wherein said substances on which the protocol was performed are analysed directly on the mobile analysis support.

22. The process according to claim 19, wherein said substances on which the protocol was performed are analysed after their transfer from the mobile analysis support.

23. The process according to claim 17, further comprising delivering to the mobile analysis support from the means for delivering the substances to be analysed liquid drops containing the substances to be analysed; and
   passing the liquid drops containing the substances to be analysed in front of the means for delivering the reagents.

24. A system to perform a biological, chemical or biochemical protocol in continuous flow on substances to be analysed comprising:
   a mobile analysis support comprising means of reception of substances to be analysed and reagents, wherein the reception means are arranged so as to form a matrix of rows and columns;
   a mechanism connected to the support, where the mechanism moves with a continuous movement or in small steps thereby enabling each column in the reception means to pass in front of one or more different elements necessary to perform the protocol;
   a liquid film covering the reception means, where the liquid film is immiscible with the substances to be analysed and the reagents, thereby preventing the evaporation of the substances to be analysed and the reagents;
   means of delivering the substances to be analysed to the reception means,
   means of delivering the reagents to the reception means; and
   heating means arranged such that while the protocol is being carried out each column in the reception means passes in front of the heating means after passing in front of the means of delivering the reagents, thereby bringing the reception means to different determined temperatures successively, wherein
   the means of delivering the substances to be analysed is between the means of delivering the reagents and the heating means.

25. A system to perform a biological, chemical or biochemical protocol in continuous flow on substances to be analysed comprising:
   a mobile analysis support comprising means of reception of substances to be analysed and reagents, wherein the reception means are arranged so as to form a matrix of rows and columns;
   a mechanism connected to the support, where the mechanism moves with a continuous movement or in small steps thereby enabling each column in the reception means to pass in front of one or more different elements necessary to perform the protocol;
   a liquid film covering the reception means, where the liquid film is immiscible with the substances to be analysed and the reagents, thereby preventing the evaporation of the substances to be analysed and the reagents;
   means of delivering the reagents to the reception means;
   heating means arranged such that while the protocol is being carried out each column in the reception means passes in front of the heating means after passing in front of the means of delivering reagents, thereby bringing the reception means to different determined temperatures successively; and
   detection means for the substances on which the protocol has been performed, thereby providing an analysis of these substances, wherein
   the heating means is between the means of delivering the reagents and the detection means.

26. A process for performing a biological, chemical or biochemical protocol in continuous flow on substances to be analysed, wherein said process is carried out with a system according to claim 25, and said process comprises:
   moving the mobile analysis support,
   implementing the protocol on substances to be analysed while the mobile analysis support is moving, by the input of the thermal energy supplied by the heating means.

27. The process according to claim 26, further comprising delivering to the mobile analysis support from the means for delivering the substances to be analysed liquid drops containing the substances to be analysed; and
   passing the liquid drops containing the substances to be analysed in front of the means for delivering the reagents.

* * * * *